United States Patent
Masuda et al.

(12) 
(10) Patent No.: US 6,800,248 B1
(45) Date of Patent: Oct. 5, 2004

(54) METHOD FOR CLEANING A DIALYZER HEMODIALYSIS SYSTEM

(75) Inventors: Toshiaki Masuda, Osaka (JP); Yukari Masuda, Osaka (JP)

(73) Assignee: Nipro Corporation, Osaka (JP)

( * ) Notice: Subject to any disclaimer, the term of this patent is extended or adjusted under 35 U.S.C. 154(b) by 289 days.

(21) Appl. No.: 09/787,626

(22) PCT Filed: Jul. 21, 2000

(86) PCT No.: PCT/JP00/04913

§ 371 (c)(1),
(2), (4) Date: Mar. 21, 2001

(87) PCT Pub. No.: WO01/07099

PCT Pub. Date: Feb. 1, 2001

(30) Foreign Application Priority Data

Jul. 22, 1999 (JP) .......................................... 11-207276

(51) Int. Cl.[7] ............................................... A61L 2/18
(52) U.S. Cl. .......................................... 422/28; 205/626
(58) Field of Search ........................... 422/28, 44, 292; 210/646, 760; 205/626, 746

(56) References Cited

U.S. PATENT DOCUMENTS 5,759,489 A * 6/1998 Miura et al. .................. 422/28
6,379,617 B1 * 4/2002 Spickermann ................ 422/44
2003/0080467 A1 * 5/2003 Andrews et al. ............ 264/275

FOREIGN PATENT DOCUMENTS

JP          11012774 A    *    1/1999
WO      WO 99/29929    *    6/1999

* cited by examiner

*Primary Examiner*—Elizabeth McKane
(74) *Attorney, Agent, or Firm*—Kobovcik & Kubovcik

(57) ABSTRACT

A method for cleaning a hemodialysis system after completion of dialysis, characterized in that ozone water produced by an apparatus for producing high concentration ozone water 5 and having an average ozone concentration of not less than 15 ppm is sequentially guided to dialysate pipes of a hemodialysis system 4 after completion of dialysis including a water supply tube for dialyzing water 40, a water supply tube for dialysate 41 and a water drainage tube for dialysate 42; and ozone water having an average ozone concentration of not less than 2 ppm is drained from the water drainage tube 42. It is possible to prevent carbonates, proteins, biofilms and the like from adhering so that cleaning with excellent sterilizing property can be realized.

2 Claims, 3 Drawing Sheets

METHOD FOR CLEANING A DIALYZER HEMODIALYSIS SYSTEM

TECHNICAL FIELD

The present invention relates to a method for cleaning dialysate pipes in a hemodialysis system after completion of dialysis, and more particularly to a method for cleaning a hemodialysis system that is effective for preventing carbonates, proteins, bio-films and the like from adhering and is excellent in sterilizing property.

BACKGROUND ART

"Dialysis" is a therapeutic method in which, by combining the principles of diffusion and osmosis or filtration, aetiologic substances existing in a body fluid are brought into contact with a dialysate and removed, thereby maintaining the homeostasis of the body fluid. This therapeutic method comprises: guiding the blood of a patient to the outside of the body; causing the blood to pass through an artificial kidney (dialyzer) which carries out dialysis; bringing the blood and a dialysate into contact with each other via a semi-permeable membrane in the artificial kidney; causing aetiologic substances contained in the blood to move into the dialysate; and returning the blood thus cleaned into the body of the patient.

"Hemodialysis system" generally comprises: a pipe for guiding dialyzing water, which is connected with an artificial kidney for carrying out blood dialysis, blood filtration, blood filtration dialysis or the like; a pipe for guiding a dialysate in which a chemical for dialysis is dissolved into the dialyzing water; a pipe for draining the dialysate; flow rate controlling pumps interposed therebetween and the like. The pipes for guiding dialysate mainly include: a pipe for supplying dialyzing water; a water supply tube for supplying the artificial kidney with the dialysate in which a chemical for dialysis is dissolved in the dialyzing water; and a water drainage tube for draining the dialysate from the artificial kidney. After connecting (1) a line for guiding blood of a patient to the artificial kidney, (2) the artificial kidney and (3) a line for returning the blood having been dialyzed through the artificial kidney to the patient, dialysis is carried out. After completion of dialysis, the artificial kidney and the lines for blood that are connected to the artificial kidney in Japan are disposed of. Meanwhile, the pipes for the dialyzing water and the dialysate are cleaned and recycled. Cleaning of these pipes is generally accomplished by connecting the pipes removed from the artificial kidney with a coupler connector and causing a cleaning solution to flow therethrough.

Heretofore, for the purpose of cleaning dialysate pipes in a hemodialysis system, reagents such as sodium hypochlorite, acetic acid, and peracetic acid have been used. Although cleaning by the use of such reagents can sterilize microorganisms, there is a case that calcium carbonate and proteins are adhered to the pipe portions of the hemodialysis system, and moreover there is a case that bio-films (mixed layers composed of dead bacteria, calcium carbonate and the like) are gradually accumulated. Such bio-films are very difficult to be removed once having adhered to the pipes. In order to prevent these carbonates, proteins and bio-films from adhering, cleaning is carried out by alternately using plural reagents having different characteristics.

Meanwhile, in Japanese Unexamined Patent Publication JP-A 7-171212 (HEI-7, 1995) which discloses simplifying a dialysis drainage operation, a method for cleaning an artificial hemodialysis therapeutic system which utilizes ozone water and an apparatus for implementing the method are disclosed. In this method, ozone is generated from RO water by an apparatus for producing ozone which generates ozone in response to the RO water, then the RO water and the ozone are mixed again to form ozone water, and thereafter a cleaning operation of the dialysate pipes in the artificial hemodialysis therapeutic system is carried out. In the above method, the RO water is purified from raw water at an apparatus for producing pure water 1. The ozone is generated in an electrobath 10 of an apparatus for producing ozone 2, and outputted while being separated from the RO water in a gas/liquid separating tank 11. In the case of a cleaning operation, the RO water from the apparatus for producing pure water 1 and the ozone from the apparatus for producing ozone 2 are mixed and outputted as ozone water. On the other hand, in the case of dialysis therapy, the RO water from the apparatus for producing pure water 1 is outputted as it is. However, in this cleaning method, it is considered that in the course of mixing the generated ozone with the RO water, the ozone itself is extinguished so that the concentration of the ozone water reaching the hemodialysis therapeutic system is necessarily relatively lower compared to that at the time of generation. Therefore, it is considered that the cleaning efficiency thereof is lower than desired.

Moreover, in the above patent publication, there is no clear description about the efficiency of preventing adhesion of carbonates, proteins, bio-films and the like, and about the optimum ozone concentration of the ozone water.

The present invention has been made in consideration of the above problems, and it is an object of the present invention to provide a method for cleaning dialysate pipes of a hemodialysis system using high concentration ozone water, which is effective for preventing adhesion of carbonates, proteins, bio-films and the like and excellent in sterilizing property.

DISCLOSURE OF THE INVENTION

As a result of due consideration for achieving the above-mentioned object, the inventors of the present invention have found that adhesion of calcium carbonate, proteins, bio-films and the like to the dialysate pipes of the hemodialysis system can be prevented, while realizing cleaning with an excellent sterilizing property, when an apparatus for producing high concentration ozone water is used as the apparatus for producing ozone, and a setting is made to achieve an average ozone concentration at the time of draining ozone water of less than 2 ppm. These findings led to the present invention.

More specifically, the present invention is a method for cleaning a hemodialysis system after completion of dialysis, characterized in that ozone water generated by an apparatus for producing high concentration ozone water is sequentially introduced after completion of dialysis to dialysate pipes of the hemodialysis system including a water supply tube for supplying dialyzing water, a water supply tube and a water drainage tube for dialysate, and then the ozone water is drained from the water drainage tube.

Also, the present invention is a method for cleaning a hemodialysis system in which cleaning is carried out by using high concentration ozone water generated by the water electrolytic process, characterized in that an average ozone concentration at the time of draining the ozone water is not less than 2 ppm.

Figure 1:
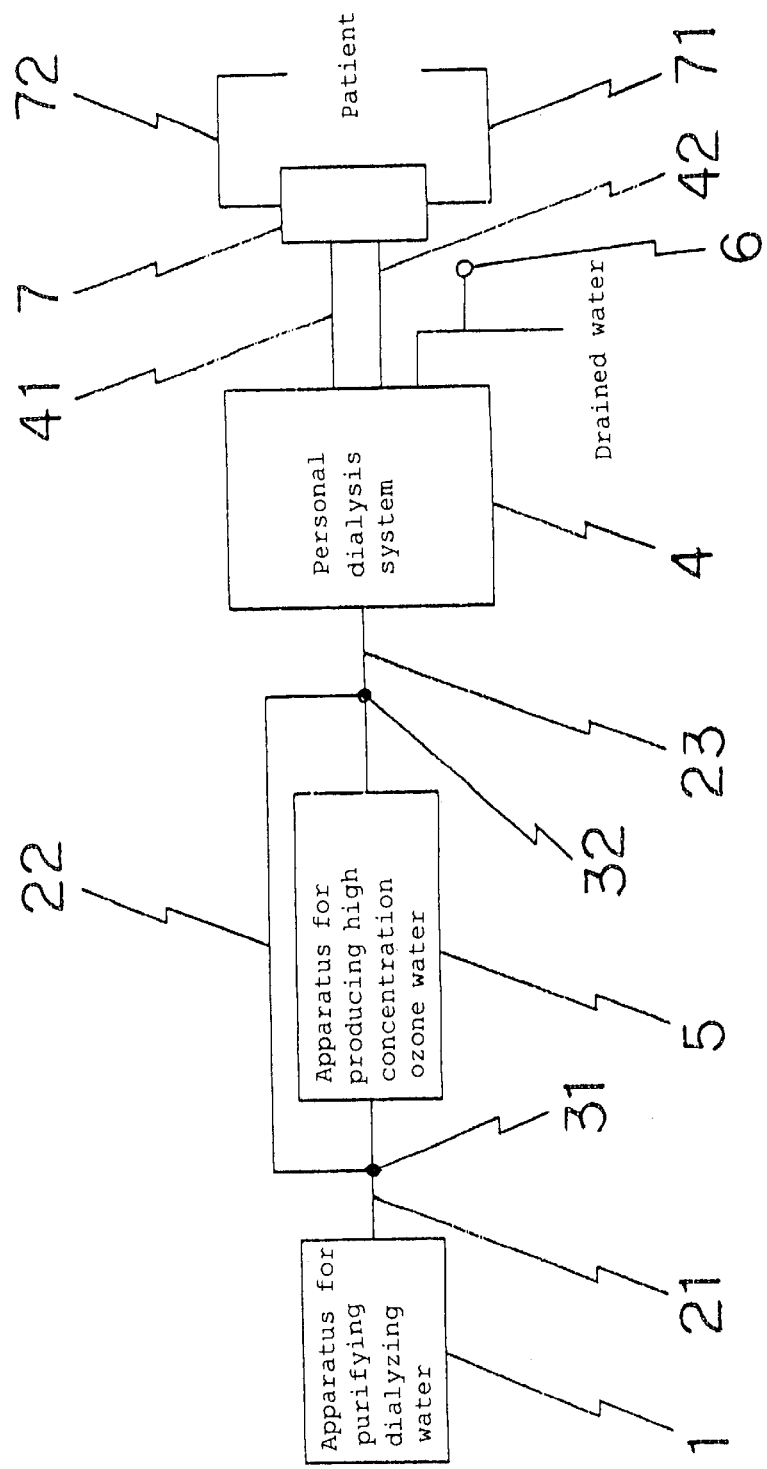
FIG. 1 is an explanatory view of a method for cleaning a hemodialysis system according to the present invention.

In the drawings, the reference numeral 1 denotes an apparatus for purifying dialyzing water; the reference numerals 21 and 23 denote passages; the reference numeral 22 denotes a by-pass; the reference numerals 31 and 32 denote change-over valves; the reference numeral 4 denotes a personal dialysis system; the reference numeral 40 denotes a water supply tube for dialyzing water; the reference numeral 41 denotes a water supply tube for dialysate; the reference numeral 42 denotes a water drainage tube for dialysate; the reference numeral 43 denotes a pump; and the reference numeral 44 denotes an apparatus for supplying a chemical for dialysis. The reference numeral 5 denotes an apparatus for producing high concentration ozone water; the reference numeral 6 denotes an outlet detection part; the reference numeral 7 denotes an artificial kidney; the reference numeral 71 denotes a blood inlet line; and the reference numeral 72 denotes a blood return line.

BEST MODE FOR CARRYING OUT THE INVENTION

Figure 3:
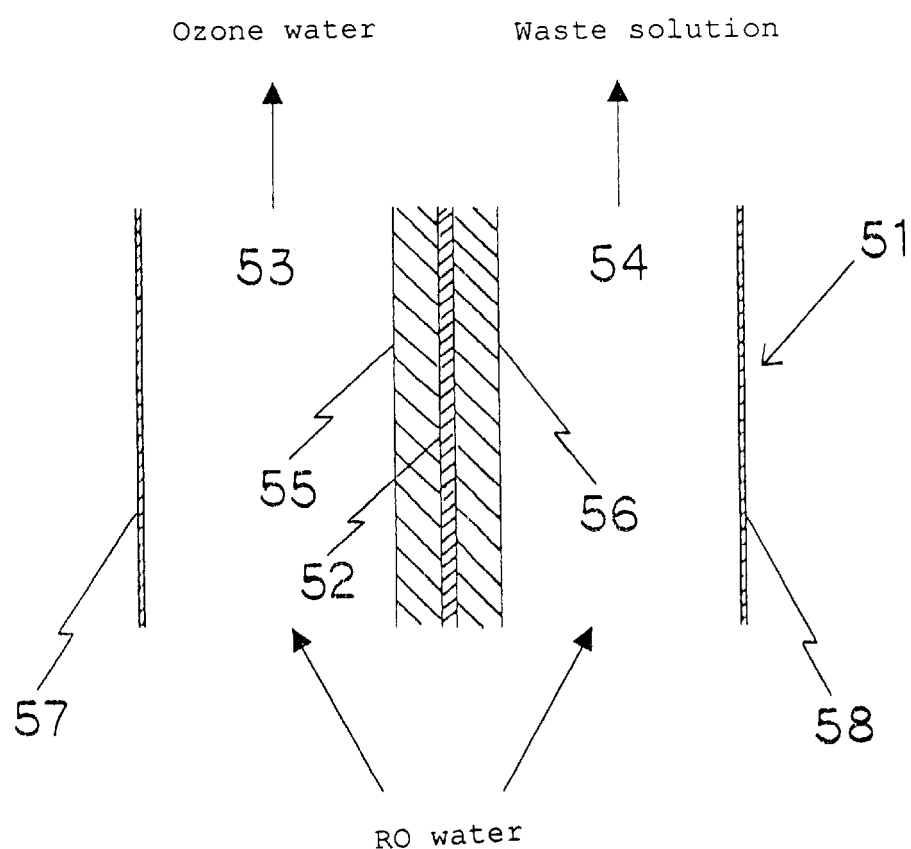
FIG. 3 is an explanatory view of one example of an apparatus for producing high concentration ozone water for use in the present invention.

An apparatus for producing high concentration ozone water 5 for use in the present invention is an apparatus that generates ozone water by a water electrolytic process. For instance, as shown in FIG. 3, the interior of a casing 51 is partitioned into a positive electrode chamber 53 and a negative electrode chamber 54 by means of an electrolytic membrane of high-molecular substance 52; a noble metal catalyst for positive electrode (such as platinum) 55 and a noble metal catalyst for negative electrode (such as platinum and silver) 56 are disposed on the surfaces of the electrolytic membrane of the high-molecular substance 52 of the positive electrode chamber 53 side and the negative electrode chamber 54 side, respectively, so that these catalysts contact the surfaces of the high-molecular substances 52; an inlet for raw water and an outlet are provided for each of the positive electrode chamber 53 and the negative electrode chamber 54; and a DC power supply is connected between a positive electrode 57 and a negative electrode 58 (WO99/29929). Preferably, the noble metal catalyst having ozone generation catalytic activity (such as platinum) is formed into a wire netting. Alternatively, as disclosed in Japanese Unexamined Patent Publication JP-A 11-33449 (HEI-11, 1999), a positive electrode chamber and a negative electrode chamber are provided with a solid electrolytic membrane being interposed therebetween, and each of the positive electrode chamber and the negative electrode chamber is provided with an electrode comprising wire netting and a lath net having a roughly rhomboid opening arranged sequentially from the side of the solid electrolytic membrane to form a water pathway.

In the apparatus for producing high concentration ozone water 5 as described above, it is possible to obtain ozone water of high concentration (50 ppm at the maximum) by directly electrolyzing tap water.

In the present invention, "ozone water" refers to high concentration ozone water generated by the above-mentioned apparatus for producing high concentration ozone water 5, and does not refer to that in which ozone having been separated from generated ozone water is mixed into pure water again.

Dialyzing water such as, for example, RO water is directly injected into the inlet for raw water of the above-mentioned apparatus for producing high concentration ozone water 5, and ozone water is discharged from the outlet for ozone water of the same apparatus. The concentration of the ozone to be discharged is generally not less than 15 ppm. This is not particularly limited as a condition in generating ozone water.

The hemodialysis system according to the present invention generally refers to the system other than the artificial kidney 7, the blood inlet line 71 for guiding blood into the artificial kidney 7 from a patient, and the blood return line 72 for returning the blood from the artificial kidney 7 to the patient, and which comprises: a pipe for guiding a dialysate to the artificial kidney 7; a pipe for draining the dialysate; and a flow rate controlling pump interposed between these pipes. As used herein, the personal dialysis system 4 refers to a system having functions of dissolving a chemical for dialysis in dialyzing water to prepare a dialysate, transferring the dialysate to the artificial kidney, and circulating the blood and the dialysate while monitoring the condition of the patient undergoing the dialysis. And to this system, lines for blood and the artificial kidney are connected for carrying out dialysis of blood.

As used herein, the dialysate pipes of the hemodialysis system include a pipe for providing a dialysate and a pipe for draining the dialysate, and more specifically, a water supply tube for guiding dialyzing water (water supply tube for dialyzing water 40), a water supply tube for guiding a dialysate which is prepared by dissolving a chemical for dialysis in the dialyzing water (water supply tube for dialysate 41), and a drainage tube for draining the dialysate (water drainage tube for dialysate 42). Each pipe usually has a diameter of 5 to 10 mm, preferably 6 to 8 mm, and a length of 200 to 1000 cm, preferably 400 to 800 cm. The material for forming each pipe is generally a plastic such as silicone.

At the time of cleaning the hemodialysis system, after removing two kinds of pipes (the water supply tube for dialysate 41 and the water drainage tube for dialysate 42) from the artificial kidney 7, both pipes are connected with each other directly or via a coupler connector 46. Ozone water produced by the above-mentioned apparatus for producing high concentration ozone water 5 is directly introduced into the inlet of the water supply tube for dialyzing water 40. The ozone water removes substances to be removed which are adhered to the pipes while flowing from the water supply tube for dialyzing water 40 of the hemodialysis system to the water drainage tube for dialysate 42 through the water supply tube for dialysate 41. On the other hand, conversion from ozone to water rapidly advances as the ozone water flows. Therefore, in order to allow sterilization and to prevent adhesion of the carbonates, organic materials and the like in the dialysate pipes of the hemodialysis system or to remove the same by dissolving, it is necessary that the ozone concentration is high, and in the present invention, an average ozone concentration at the time of introduction is not less than about 15 ppm.

In addition, for draining the ozone water from the dialysate pipes of the system, it is necessary that the concentration of the ozone water is not less than 2 ppm. For achieving this, the ozone concentration is maintained by adjusting the time in which the ozone water passes through and the passing amount depending on the diameter and length of the pipes. More specifically, in the case of a plastic pipe having a diameter of 5 to 10 mm, preferably 6 to 8 mm, and a length of 200 to 1000 cm, preferably 400 to 800 cm, the ozone water is adjusted to flow at a rate of 200 to 1000 ml, preferably 400 to 500 ml per minute, for 10 to 60 minutes, preferably 15 to 30 minutes. Adjustment of the flow rate is accomplished by means of a flow rate controlling pump located between the pipes. If the ozone concentration at the time of drainage is less than 2 ppm, carbonates, proteins, bio-films and the like are adhered to the inside of the dialysate pipes of the hemodialysis system.

Next, working examples of the present invention will be described with reference to the drawings.

Figure 2:
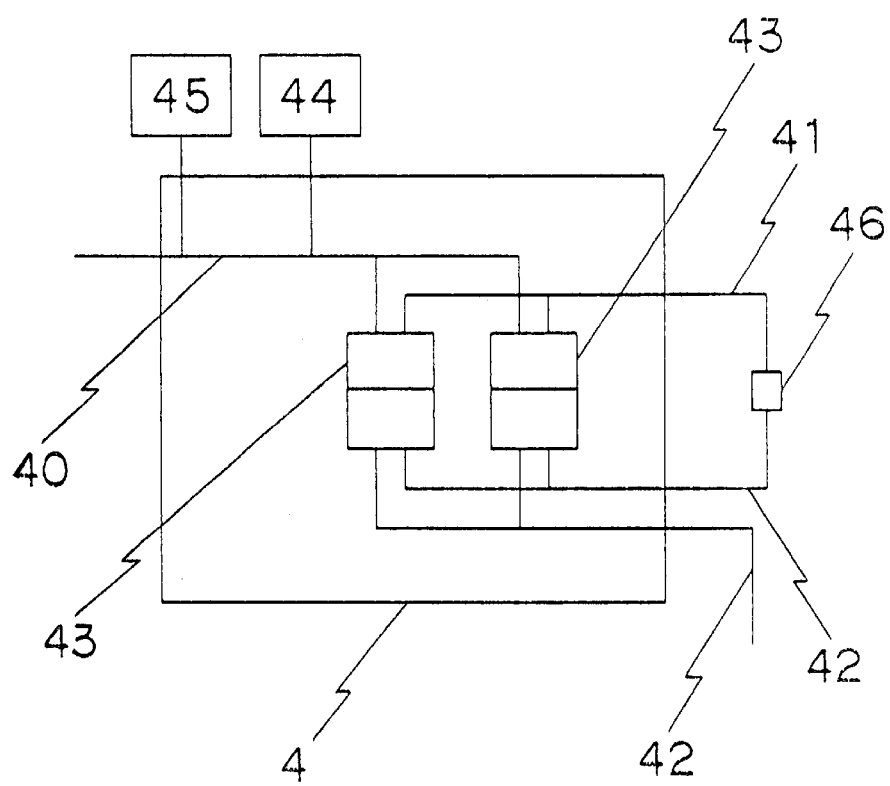
FIG. 2 is an explanatory view of one example of a hemodialysis system for use in the present invention.

Dialysis of blood according to the present invention is carried out by using, for example, the hemodialysis system as shown in FIG. 1. Dialyzing water having been purified by the apparatus for purifying dialyzing water 1 is transmitted from the passage 21 to the personal dialysis system 4 through the change-over lever 31, the by-pass 22, the change-over lever 32 and the passage 23. The personal dialysis system 4 (FIG. 2) is provided with the water supply tubes for dialyzing water 40, the water supply tube for dialysate 41 for supplying the artificial kidney 7 with the dialysate and the water drainage tube 42 for draining the dialysate from the artificial kidney 7, and then the dialysate drained from the water drainage tube 42 is discharged outside the dialysis system 4. To the artificial kidney 7 are connected the blood inlet line 71 for guiding blood derived from a patient's body and the blood return line 72 for returning the blood from the artificial kidney to the patient's body. The personal dialysis system 4 includes: the water supply tube for dialyzing water 40 following the passage 23; the water supply tube for dialysate 41 for supplying a dialysate in which a chemical for dialysis is dissolved in the dialyzing water supplied from the water supply tube 40; the water drainage tube for dialysate 42 for draining the dialysate; and the pump 43 located between the water supply tube for dialysate 41 and the water drainage tube for dialysate 42. An apparatus for supplying a chemical for dialysis 44 may exist inside the dialysis system 4. The dialysis system 4 may additionally be provided with an apparatus for introducing a cleaning solution 45.

For cleaning the dialysate pipes of the personal dialysis system 4, the artificial kidney 7, the blood inlet line 71 and the blood return line 72 are removed from the personal dialysis system 4. After that, the water supply tube for dialysate 41 and the water drainage tube for dialysate 42 are connected with each other directly or via the coupler connector 46. Then, the ozone water having passed through the passage 21, the change-over valve 31, the apparatus for producing high concentration ozone water 5, the change-over valve 32 and the passage 23 is guided to the pipes of the personal dialysis system 4 (other than the artificial kidney), namely to the water supply tube for dialyzing water 40, the water supply tube for dialysate 41 and the water drainage tube for dialysate 42, and continuously drained. During this operation, pipes 40, 41 and 42 are cleaned.

The apparatus for purifying dialyzing water 1 removes impurities from the tap water, thereby purifying the dialyzing water. This dialyzing water is mixed with a chemical for dialysis to evolve into a dialysate at the time of dialysis, whereas at the time of cleaning, is supplied to the apparatus for producing high concentration ozone water 5 to evolve into high concentration ozone water.

On the downstream side of the passage 21 connected with the apparatus for purifying dialyzing water 1, the change-over valve 31 is provided, which is configured to open toward the by-pass 22 side at the time of dialysis and toward the apparatus for producing high concentration ozone water 5 at the time of cleaning.

Also, at the confluent point located downstream of the bypass 22 and the apparatus for producing high concentration ozone water 5, is provided the change-over valve 32 which is so configured that when the change-over valve 31 opens toward the by-pass 22, the change-over valve 32 also opens toward the by-pass 22, and when the change-over valve 31 opens toward the apparatus for producing high concentration ozone water 5, the change-over valve 32 also opens toward the apparatus for producing high concentration ozone water 5.

As described above, the apparatus for producing high concentration ozone water 5 is an apparatus utilizing a water electrolytic process in which high concentration ozone water is generated by directly electrolyzing water. One example of this is shown in FIG. 3.

By using the apparatus for producing ozone water 5 based on the water electrolytic process, it is possible to produce high concentration (not less than about 15 ppm) ozone water continuously and easily at a rate of several liters per minute, so that it is possible to ensure an average ozone concentration at the time of drainage of at least 2 ppm. As shown in working examples which will be described below, if the average ozone concentration at the time of drainage of ozone water is less than 2 ppm, undesired results will be caused such as propagation of bacteria and adhesion of proteins.

Incidentally, since the ozone forming the ozone water does not have a residual property, the concentration thereof decreases with the passage of time and finally the ozone becomes oxygen which is released to the air to become natural water, so that no problems regarding pollution arise as a result of disposal.

Next, concrete examples in which the dialysate pipes of a hemodialysis system were practically cleaned by the use of the hemodialysis system as shown in FIG. 1 will be shown.

EXAMPLES 1 TO 3

After connecting artificial kidney 7 and the blood lines 71 and 72 to the personal dialysis system 4 (NUC-11, manufactured by NIPRO & Co., Ltd), blood was derived from the body of a patient suffering from chronic renal insufficiency, the blood was fed via the blood inlet line 71 to the artificial kidney 7 where it was subjected to dialysis, and then the blood was returned to the body of the patient via the blood return line 72. The time required for the dialysis was about 4 hours. After removing the artificial kidney 7 and the blood lines 71 and 72 from the personal dialysis system 4 (NUC-11, manufactured by NIPRO & CO., Ltd) used for the dialysis of the blood, the dialysate pipes 41 and 42 were directly connected with each other, and the water supply tube for dialyzing water 40, the water supply tube for dialysate 41 and the water drainage tube for dialysate 42 were cleaned by allowing the ozone water to flow from the water supply tube for dialyzing water 40 of the personal dialysis system 4. The apparatus for producing high concentration ozone water 5 (D-ozone, manufactured by Shinko Plant Engineering & Construction. Co., Ltd) continuously produced ozone water having a designated ozone concentration (inlet concentration at the personal dialysis system 4) of about 15 ppm, 20 ppm or 25 ppm and supplied the personal dialysis system 4 with the produced ozone water.

The operation process comprised: washing for 30 minutes before dialysis; connecting of the artificial kidney 7 and the blood lines 71 and 72 to the personal dialysis system 4; dialysis for about 4 hours; removing of the artificial kidney and the blood lines; connection of the dialysate pipes 41 and 42 with the coupler connector 46; washing for 30 minutes; cleaning with the ozone water for 20 minutes; and washing for 30 minutes. Such a dialysis operation was repeated once a day for 12 days.

The respective ozone concentrations of the ozone water 10 minutes, 15 minutes, and 20 minutes after starting of the cleaning with ozone water were measured by the outlet detection part 6 provided in the water drainage tube for dialysate 42, of the personal dialysis system 4; and after the cleaning, presence of adhesion of bacteria, carbonates and proteins in the water supply tube for dialysate 41 and the water drainage tube for dialysate 42 of the personal dialysis system 4, as well as degree of pollution of the water drainage tube for dialysate 42, were measured by the use of a blood leak detector (which is provided within the personal dialysis system 4. This blood leak detector measures blood leak concentration on the basis of change in permeability of light. However, the indication value also varies due to fouling in the measuring portion even if there is no leaked blood.). The results (average values, n=12) are shown in Table 1.

COMPARATIVE EXAMPLE 1

Ozone water having an ozone concentration of about 10 ppm was continuously produced by the apparatus for producing high concentration ozone water (D-ozone, manufactured by Shinko Plant Engineering & Construction. Co., Ltd), and then cleaning and the respective measurements were carried out in the same manner as Example 1. The results (n=12) are shown in Table 1.

TABLE 2

|  | Concentration (ppm) | Cleaning time (min) | Indication of blood leak detector (ppm) | Bacteria | Carbonates | Proteins |
|---|---|---|---|---|---|---|
| Comparative Example 2 (peracetic acid) | 200 | 30 | 415 | − | − | + |
| Comparative Example 3 (sodium hypochlorite) | 1000 | 30 | 378 | − | + | − |

It was found from Table 2 that when the dialysate pipes 41 and 42 were cleaned by using the cleaning solution containing peracetic acid or sodium hypochlorite, these dialysate pipes were much more polluted than those cleaned by using the ozone water. In addition, when the cleaning was carried out by using the cleaning solution containing sodium hypochlorite, adhesion of carbonates (carbonates need to be removed by cleaning using acids such as acetic acid) was observed.

From the results of Tables 1 and 2, it has been proved that adhesion of substances including bacteria, carbonates and

TABLE 1

|  | Ozone concentration (ppm) | | | | Indication of blood leak detector (ppm) | Bacteria | Carbonates | Proteins |
|---|---|---|---|---|---|---|---|---|
|  | Inlet concentration | Outlet concentration 10 minutes | Outlet concentration 15 minutes | Outlet concentration 20 minutes | | | | |
| Example 1 | 15.0 | 2.7 | 3.2 | 3.1 | 35 | − | − | − |
| Example 2 | 20.0 | 3.8 | 4.3 | 4.1 | 33 | − | − | − |
| Example 3 | 25.0 | 5.2 | 4.9 | 5.2 | 23 | − | − | − |
| Comparative Example 1 | 10.0 | 1.9 | 1.7 | 2.0 | 58 | + | − | + |

It was found from Table 1 that as the ozone concentration decreases, the water supply tube for dialysate 41 and the water drainage tube for dialysate 42 are more polluted. Incidentally, when the indication value of the blood leak detector is less than 50 ppm, it can be understood that there is little pollution.

In the case where the ozone concentration at the outlet detection part 6 (at the time of water drainage) is less than 2 ppm, adhesion of bacteria (bacteria and fungus) and proteins was determined.

COMPARATIVE EXAMPLES 2 AND 3

Cleaning and the respective measurements were carried out in the same manner as Example 1 except that cleaning of the dialysate pipes 41 and 42 was carried out by using a cleaning solution having a peracetic acid concentration of 200 ppm (Comparative Example 2) and a cleaning solution having a sodium hypochlorite concentration of 1,000 ppm (Comparative Example 3), and the cleaning time with these cleaning solutions was set at 30 minutes. The results (n=12) are shown in Table 2.

proteins can be prevented by cleaning the dialysate pipes 40, 41 and 42 of the dialysis system by the use of the ozone water having an average ozone concentration at the time of water drainage of at least 2 ppm.

EXAMPLE 4

Blood dialysis for 4 hours was carried out on a patient suffering from chronic renal insufficiency once a day, for three months in the same manner as Example 1. For each dialysis operation, after removing the artificial kidney 7 and the blood lines 71 and 72 from the personal dialysis system 4 (NCU-11, manufactured by NIPRO & CO., LTD) used for the blood dialysis, the dialysate pipes 41 and 42 were connected with each other by the coupler connector 46, and cleaned with the high concentration ozone water. The apparatus for producing high concentration ozone water 5 (D-ozone, manufactured by Shinko Plant Engineering & Construction. Co., Ltd) continuously produced ozone water having a designated ozone concentration (inlet concentration at the personal dialysis system 4) of about 25 ppm and supplied the personal dialysis system 4 with the produced ozone water. The operation process comprised: washing for 30 minutes before dialysis; dialysis for 4 hours; washing for 30 minutes after removing of the artificial kidney 7 and the blood lines 71 and 72; cleaning for 20 minutes with ozone water; and washing for 30 minutes.

After completion of each cleaning with the ozone water, presence of adhesion of bacteria, carbonates and proteins in the water supply tube for dialysate 41 and the water drainage tube for dialysate 42 of the personal dialysis system 4, as well as degree of pollution of the pipes 41 and 42, were measured by the use of the blood leak detector. As a result of the above, no adhesion of bacteria, carbonates and proteins was observed. The indication value of the blood leak detector was always lower than 50 ppm.

EXAMPLE 5

Blood dialysis for 4 hours was carried out on a patient suffering from chronic renal insufficiency once a day, for three months in the same manner as Example 1. For each dialysis operation, after removing the artificial kidney 7 and the blood lines 71 and 72 from the personal dialysis system 4 (NCU-11, manufactured by NIPRO & CO., LTD) used for the blood dialysis, the dialysate pipes 41 and 42 were connected with each other by the coupler connector 46, and cleaned with the high concentration ozone water. The apparatus for producing high concentration ozone water 5 (D-ozone, manufactured by Shinko Plant Engineering & Construction. Co., Ltd) continuously produced ozone water having a designated ozone concentration (inlet concentration at the personal dialysis system 4) of about 15 ppm and supplied the personal dialysis system 4 with the produced ozone water. The operation process comprised: washing for 30 minutes before dialysis; dialysis for 4 hours; washing for 30 minutes after removing of the artificial kidney 7 and the blood lines 71 and 72; cleaning for 20 minutes with ozone water; and washing for 30 minutes.

After completion of each cleaning with the ozone water, presence of adhesion of bacteria, carbonates and proteins in the water supply tube for dialysate 41 and the water drainage tube for dialysate 42 of the personal dialysis system 4, as well as degree of pollution of the pipes 41 and 42, were measured by the use of the blood leak detector. As a result of the above, no adhesion of bacteria, carbonates and proteins was observed. The indication value of the blood leak detector was always lower than 50 ppm.

After a lapse of three months from the cleaning with the ozone water, the inner surface of the silicone tube of the water drainage tube for dialysate 42 of the personal dialysis system 4 was observed by using an electron microscopy. No formation of bio-films was observed as a consequence.

In the above examples, the personal dialysis system 4 was used, however, the present invention can be applied in the same manner even in the case of using a dialysate preparation system and a multi-personal dialysis system. In such a case, since the length of the pipe connecting the apparatus for producing ozone water and the vessel for waste dialysate becomes long, it is necessary to produce ozone water of higher concentration in order to achieve the average ozone concentration at the time of drainage of ozone water of at least 2 ppm.

Industrial Applicability

As described above, the cleaning method according to the present invention makes it possible to prevent adhesion of carbonates, proteins, bio-films and the like in the dialysate pipes of the dialysis system, so that a cleaning method with excellent sterilization property can be realized. Furthermore, since the ozone water does not have a residual property, it is possible to shorten the washing time with the water after the cleaning with the ozone water.

What is claimed is:

1. A method for cleaning a hemodialysis system after completion of dialysis, comprising sequentially introducing ozone water generated by an apparatus for producing high concentration ozone water and having an average ozone concentration of not less than about 15 ppm to dialysate pipes of the hemodialysis system after completion of dialysis, said dialysate pipes including a water supply tube for guiding a dialyzing water, a water supply tube for dialysate and water drainage tube for dialysate, and then draining ozone water having an average ozone concentration of not less; than about 2 ppm from the water drainage tube,
    wherein the high concentration ozone water is generated directly from water by subjecting the water to a water electrolytic process using an electrolytic membrane having a positive electrode formed of a noble metal catalyst and a negative electrode formed of a noble metal catalyst disposed on opposite surfaces of the membrane.

2. A method for cleaning a hemodialysis system comprising rinsing the system with high concentration ozone water generated by a water electrolytic process, wherein an average ozone concentration of the ozone water at the completion of rinsing is not less than 2 ppm.

* * * * *